(12) United States Patent
Teugels

(10) Patent No.: US 7,516,665 B2
(45) Date of Patent: Apr. 14, 2009

(54) DOUBLE MEMBRANE TRANSDUCER PROTECTOR

(75) Inventor: Ludwig Teugels, Miramar, FL (US)

(73) Assignee: JMS North America Corporation, Hayward, CA (US)

( * ) Notice: Subject to any disclaimer, the term of this patent is extended or adjusted under 35 U.S.C. 154(b) by 465 days.

(21) Appl. No.: 11/476,494

(22) Filed: Jun. 28, 2006

(65) Prior Publication Data

US 2007/0014689 A1    Jan. 18, 2007

Related U.S. Application Data

(63) Continuation-in-part of application No. 10/745,390, filed on Dec. 23, 2003, now Pat. No. 7,069,788.

(51) Int. Cl.
*G01L 7/00* (2006.01)
(52) U.S. Cl. ....................................... 73/706
(58) Field of Classification Search ................. None
See application file for complete search history.

(56) References Cited

U.S. PATENT DOCUMENTS

| | | | |
|---|---|---|---|
| 4,459,139 A | 7/1984 | von Reis et al. | |
| 4,493,693 A | 1/1985 | Bilstad et al. | |
| 5,500,003 A | 3/1996 | Guala et al. | |
| 5,603,792 A | 2/1997 | Guala et al. | |
| 5,641,496 A * | 6/1997 | Van Roekel | 424/404 |
| 5,772,624 A | 6/1998 | Utterberg et al. | |
| 5,914,033 A * | 6/1999 | Carlsson | 210/90 |
| 6,086,762 A | 7/2000 | Guala | |
| 6,168,653 B1 | 1/2001 | Myers | |
| 6,346,084 B1 | 2/2002 | Schnell et al. | |
| 6,536,278 B1 | 3/2003 | Scagliarini | |
| 7,069,788 B2 * | 7/2006 | Teugels | 73/706 |
| 2004/0237785 A1 | 12/2004 | Neri | |

FOREIGN PATENT DOCUMENTS

| | | |
|---|---|---|
| DE | 19816871 | 10/1999 |
| GB | 2168263 | 6/1986 |
| WO | WO 2004/082732 | 9/2004 |

* cited by examiner

*Primary Examiner*—Robert R Raevis
(74) *Attorney, Agent, or Firm*—Rutan & Tucker LLP

(57) ABSTRACT

A transducer protector including at least two spaced apart filter membranes. The transducer protector may include a body positioned between two tubular connectors, each of which contains an axially aligned lumen. The body lumen may be separated from the lumen of each of the tubular connectors, respectively, by the filter membranes. An indicator may be disposed in the body to alert a user that the filter membrane has been breached by a contaminant so that the user can take immediate steps to prevent further contamination of the system. The indicator may display a change in an absorbance spectra peak at a wavelength ranging from approximately 200 nm to approximately 800 nm upon reacting with bodily fluid.

20 Claims, 4 Drawing Sheets

DOUBLE MEMBRANE TRANSDUCER PROTECTOR

CROSS-REFERENCE TO RELATED APPLICATIONS

This application is a continuation-in-part of U.S. patent application Ser. No. 10/745,390, filed Dec. 23, 2003, now U.S. Pat. No. 7,069,788, which is incorporated into this application as if fully set forth herein.

BACKGROUND OF THE INVENTION

Hemodialysis, the most frequently used method for treating advanced and chronic kidney failure consists of a continuous process of removing blood from a patient, cleansing the blood with a special filter mounted on a dialysis machine, and returning the cleansed blood back to the patient. During the hemodialysis procedure, a trained health-care professional will continuously monitor the arterial (pre- and/or post-pump) and venous pressure in the extracorporeal circuit. This is typically done through a tube positioned between the extracorporeal circuit and the dialysis machine. A transducer protector is an in-line sterile barrier and is recommended to be placed between the monitoring line and the dialysis machine. The main purpose of the transducer protector, if correctly used, is to prevent cross-contamination between patients. With dialysis machines, blood must be contained to the extracorporeal circuit, while the safe operation of the dialysis session depends on the ability to accurately measure the pressure in the extracorporeal circuit. The hydrophobic nature of the membrane in the transducer protector prevents fluid (e.g., blood) from passing through the membrane while allowing air to flow freely across the membrane, facilitating accurate pressure measurements. At the end of the dialysis session, the transducer protector and the extracorporeal circuit (blood tubing sets) are discarded and replaced by a new sterile set for the next dialysis sessions.

The transducer protector generally includes two components sealed around a filtering hydrophobic membrane, which acts as a sterile barrier. The two components can be any combination of a male-male, female-female and male-female connectors that attach to medical equipment. The transducer protector is believed to be essential in shielding the dialysis equipment and patients from risks of contamination by infected blood. Typical transducer protector devices are described, for example, in U.S. Pat. Nos. 5,500,003 and 5,603,792 to Guala et al.; U.S. Pat. No. 6,086,762 to Guala; U.S. Pat. No. 6,168,653 to Myers and U.S. Pat. No. 6,536,278 to Scagliarini, each of which is incorporated by reference into this application as if fully set forth herein. These references disclose transducer protectors of various configurations, but with the common features described above of a single filtering membrane between two tubular connectors.

Due to the high risk of blood contamination and incidents involving wetted/breached membranes in transducer protectors, which can occur due to fluctuation of fluid levels in the arterial and/or venous drip chamber, as well as due to changes of pressures in the extracorporeal circuit, it has become necessary to provide further protection between the pressure-sensing port of the hemodialysis machine and the extracorporeal circuit. Proposals for further protection include placing one or more redundant transducer protectors in the system and/or utilizing transducer protectors with luer extensions so that visual inspection of failure is facilitated. However, potential drawbacks to proposed solutions include, but are not limited to, the fact that they are bulky to use, they offer increased risk of non-sterile procedures, and they generally employ poor connections between the different transducer protectors.

Applicants have recognized that it would be desirable to provide a transducer protector with beneficial improvements such as greater overall protection capability, a reduction in the amount of handling and connecting required, a sustained level of connection sterility, a more precise pressure monitoring capability, and a reduction in inventory control, which provides cost savings to users.

BRIEF SUMMARY OF THE INVENTION

Accordingly, one embodiment of a transducer protector device includes a first tubular connector configured for connection to a monitoring tube that is connected to the extracorporeal circuit, a second tubular connector configured for connection to a nipple (pressure sensing port) of a dialysis machine, a body positioned between the first and second tubular connectors, a first filter member positioned between the body and the first tubular connector, and a second filter member positioned between the body and the second tubular connector.

The body and first and second tubular connectors can include axially aligned lumens and can be connected together via ultrasonic welding, heat sealing, RF welding and even self-adhesive patches. In one embodiment, the first and second tubular connectors have a luer connector end and a flanged end, the flanged end for the first and second tubular connectors each configured for mating with flanged ends on the body. The first tubular connector can have a male luer connector and the second tubular connector can have a female luer connector. However, such connector types can be reversed or both connectors can be either a male connector or a female connector. Further, the connectors can be fashioned as neither male nor female, but instead in the configuration of a slip end. Moreover, the first and second filter members can be secured in place between the mating portion of the flanged sections of the body and the first and second tubular connectors.

In one embodiment, an indicator is provided between the first and second filter members either in a lumen of the body, on a surface of the body, and/or in an area where the body and the tubular connectors meet. The indicator can be in the form of a biological or chemical material and may include the feature of changing color upon contact with a bodily fluid. The indicator can also be in the form of a sensor, which may be attached via mechanical means to the transducer protector.

In one embodiment, the indicator displays a change in an absorbance spectra peak at a wavelength ranging from approximately 200 nm to approximately 800 nm upon reacting with bodily fluid, which can include one or more blood components. The change in the absorbance spectra can be an increase or decrease in the absorbance intensity or the absorbance wavelength of the peak. Such change in an absorbance spectra peak can be detected by a clinician as a change in color, or may be detected by a sensor. It is contemplated that the indicator can be selected from the group consisting of m-cresol purple, Indigo Carmine, and Brilliant Blue G250.

In one embodiment, a transducer protector device includes a housing including spaced apart first and second filter members, and an indicator disposed in the housing between the filter members, the indicator displaying a change in an absorbance spectra peak at a wavelength ranging from approximately 200 nm to approximately 800 nm upon reacting with bodily fluid.

In another embodiment, a transducer protector device includes a first connector configured for connection to a first tube, a second connector configured for connection to a second tube, a body including a lumen positioned between the first and second connectors, a first filter member having a portion captured between a first surface of the body and the first connector, and a second filter member having a portion captured between a second surface of the body and the second connector, and an indicator disposed in the body, the indicator displaying a change in an absorbance spectra peak at a wavelength ranging from approximately 200 nm to approximately 800 nm upon reacting with bodily fluid.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Described herein is a transducer protector including more than one filter membrane so that detection of a breached or wetted membrane can lead to prevention of system contamination (in contradistinction to the prior art devices in which detection of a breached or wetted membrane could likely lead to extensive system contamination). To that end, the examples herein are directed to a transducer protector having two filter membranes that are spaced apart in a housing. The housing may include a body with a length and a connector positioned at each end of the body with each of the two filter membranes positioned respectively between the connectors and the body. It should be appreciated that although the examples and embodiments described herein are in connection with a transducer protector having two filter membranes, it is equally within the scope of the present invention for the transducer protector to contain any number of filter membranes, i.e., three, four, five, etc., to ensure that multiple barriers within a single device are provided. In a preferred embodiment, the transducer protector includes a biological and/or chemical indicator, examples of which are discussed herein, to alert a clinician or physician that a potential contaminant has bypassed the initial barrier (e.g., membrane).

By providing a single transducer protector that includes more than one filter membrane along with an optional detection system, various objectives are achieved. Notably, utilization of such a transducer protector in a system would be advantageous over systems having two or more independent transducer protectors in that, for example, there is a reduction in the necessity of handling and connecting and hence, a reduction in contamination risk caused by a non-sterile technique when connecting two or more transducer protectors, and the inventory control is reduced by at least half. Moreover, incorporating multiple filters into one device ostensibly provides cost savings to the users. Additionally, the use of one, as opposed to multiple, separate transducer protectors provides increased sterility and should enable more precise pressure monitoring.

Figure 1:
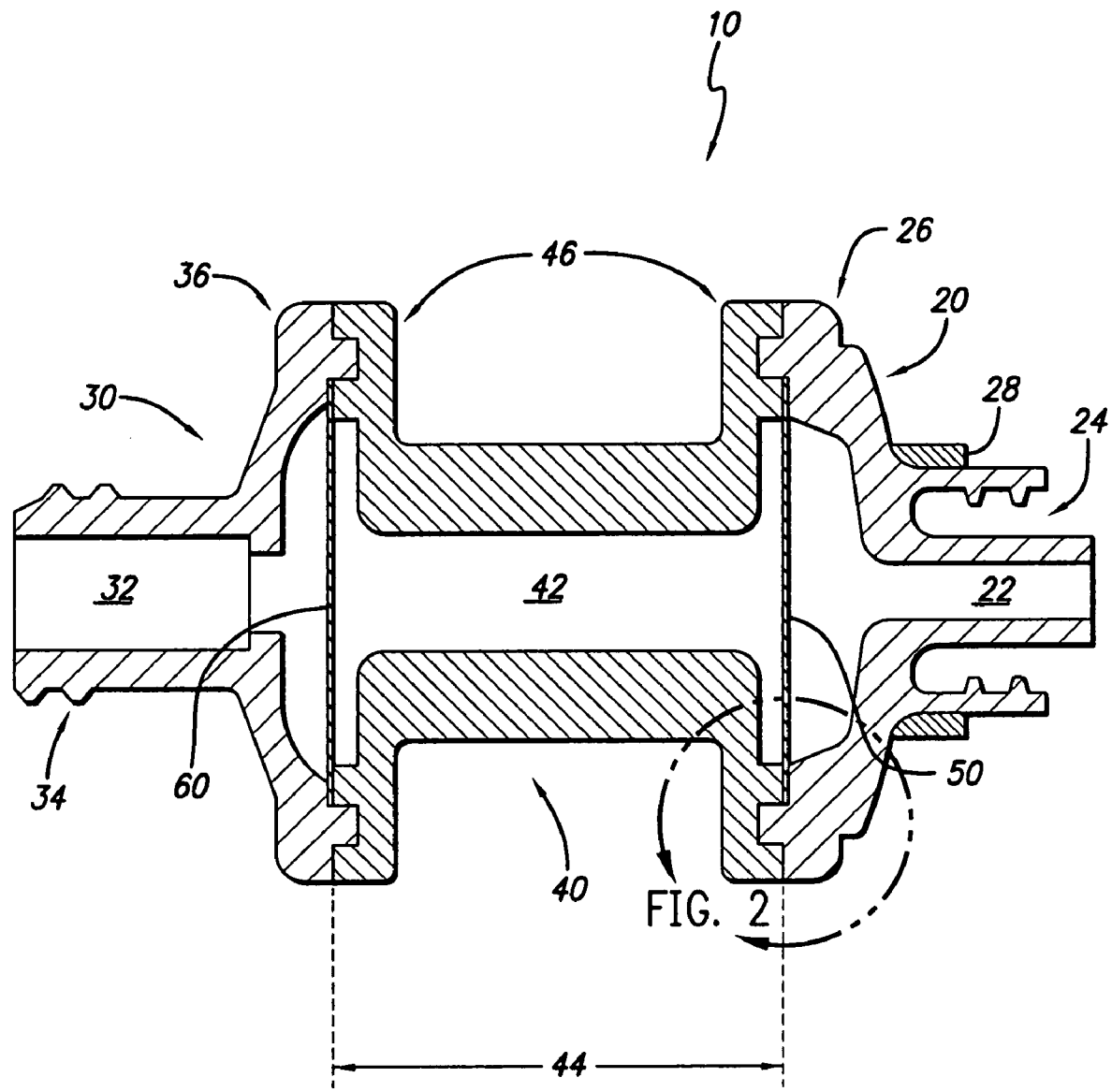
FIG. 1 is a cross-sectional view of a transducer protector.
Figure 2:
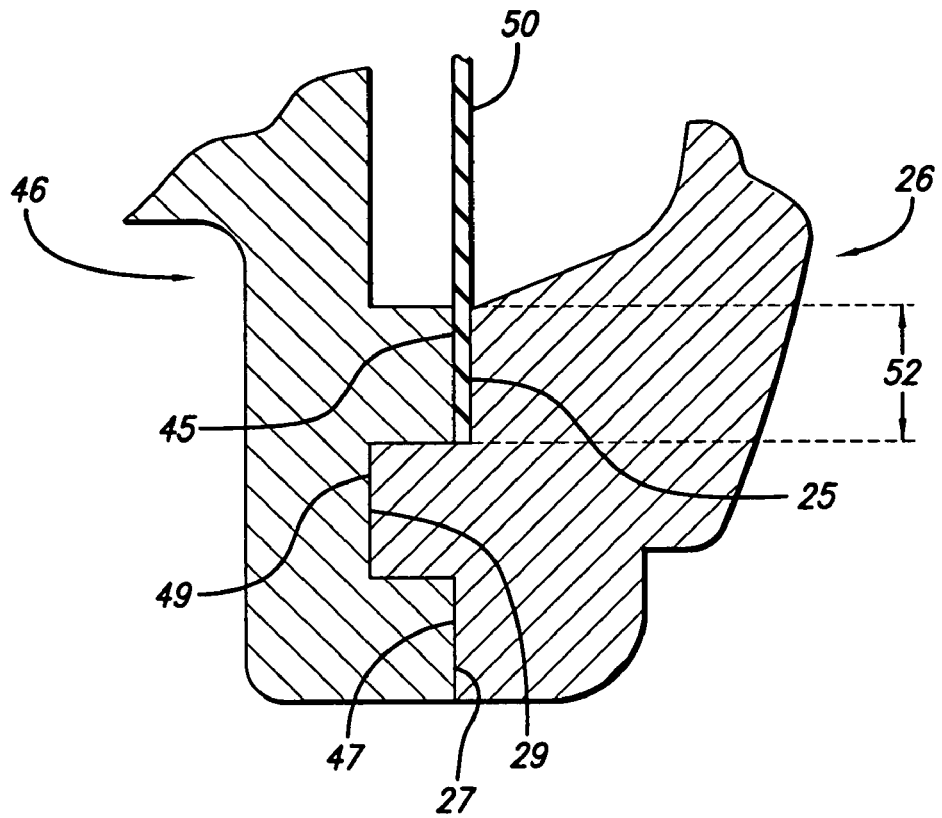
FIG. 2 is an enlarged view of section "2" indicated in FIG. 1.

Referring now to FIG. 1, a transducer protector 10 of the present invention is illustrated, having a first tubular connector 20, a second tubular connector 30 and a body 40. The first tubular connector 20 has a lumen 22 and a female luer connector 24. The first tubular connector 20 is attached to the body 40 along a flanged section 26, while the second tubular connector 30 is attached to the body 40 along a flanged section 36. The body 40 has flanged areas 46 that are configured to mate with flanged sections 26, 36. More particularly, as seen in FIG. 2 in connection with the first tubular connector 20 and the body 40, flanged section 26 contains receiving portions 25, 27 and a projection 29, which correspondingly mate with projections 45, 47 and receiving portion 49. In this embodiment, ultrasonic welding connections between the flanged sections 26 and 46 occur circumferentially along the aforementioned mating portions and projections to seal the body 40 to the first tubular connector 20. The second tubular connector 30 is likewise attached to the body 40. Of course, it should be appreciated that the body 40 could be connected to the tubular connectors 20, 30 by many other methods other than ultrasonic welding, including, but not limited to, use of adhesives, heat sealing, RF welding, and even self-adhesive patches.

As shown in FIGS. 1 and 2, between both tubular connectors 20, 30 and the body 40, there is positioned filter membranes 50, 60 respectively. Filter membranes 50, 60 can be made of PTFE (polytetrafluoroethylene), although certainly other materials such as polypropylene, PES, PVDF (polyvinylidene difluoride), acrylic copolymer and other combinations of polymeric materials, would also be suitable for forming a contaminant barrier. The filter membranes 50, 60 are attached in place at the periphery thereof, being sandwiched between the body 40 and the tubular connectors 20, 30, respectively. With reference to tubular connector 20 and body 40, the sandwiching of the filter membrane 50 occurs between receiving portion 25 and projection 45, as shown in FIG. 2. In order to ensure that filter membrane 50 is secured in place, a length 52 must be between the respective body portion and tubular connector portion (in this case, receiving portion 25 and projection 45). Of course, depending on the materials involved and method of attachment, this required length can vary. In this embodiment, length 52 is between the range of approximately 2 mm to 10 mm. It should be appreciated that filter membrane 60 is similarly secured in place along a necessary length between flanges 36 and 46.

Referring again to FIG. 1, the first tubular portion 20 is shown with a female luer connector 24, which in this embodiment is configured for connection with a male luer connector (not shown) on the sterile side of the transducer protector 10, or the side connected to the dialysis machine. The second tubular portion 30, on the other hand, is shown with a male luer connector, which in this embodiment is configured for connection with a female luer connector (not shown) on the non-sterile side of the transducer protector 10, or the side connected to a gauge or other pressure sensitive device. Of course, the connectors on either the sterile or non-sterile side can be of many different types, depending on the connection requirements of the system. First tubular connector 20 has a lumen 22, which, when connected, is in fluid communication with tubing (not shown) connected to a dialysis machine, whereas second tubular connector 30 has a lumen 32, which, when connected, is in fluid communication with tubing (not shown) connected to a pressure sensitive device.

Body 40 has a lumen 42, which in this embodiment is axially aligned with the lumens 22, 32 of the tubular connectors 20, 30 respectively. In a preferred embodiment, at least a portion of the body 40 is made of a transparent or translucent material so that the lumen 42 can be seen by the clinician or physician that is monitoring the transducer protector 10. Thus, if blood comes through lumen 22 and into contact with the filter membrane 50 and contaminant enters lumen 42, the clinician or physician will be able to take immediate action to prevent further progress of the blood or contaminant toward and in contact with the filter membrane 60. To further this goal of providing time to prevent contamination, the filter membranes 50 and 60 should be separated by a distance, which distance in this embodiment would be length 44. In the described embodiment, the optimal distance between the filter membranes 50, 60 to provide adequate warning, while maintaining an acceptable size has been found to be in the range of approximately 15 mm to 30 mm. However, depending on the materials of the parts and/or the particular application, certainly this distance could be shortened or extended and any distance would be within the scope of the present invention.

In one embodiment, a transducer protector with a first and second filter membrane was assessed in vitro. Static pressure measurements of the arterial pressure sensor and the venous pressure sensors were taken, and the results showed a generally linear relationship between measured pressure and imposed pressure between approximately +300 mm Hg and −300 mm Hg. Dynamic pressure measurements were also taken using a single needle setup and a double needle setup. A circulating solution of 55% water and 45% glycerin was used at blood flow rates of approximately 100, 200, 300, 400, and 500 ml/minute. The dynamic pressure measurements in the double needle configuration showed a mean pressure difference between the first filter membrane and the second filter membrane of less than approximately 5 mm Hg (±S.D.). The dynamic pressure measurements in the single needle configuration showed a mean pressure difference between the first filter membrane and the second filter membrane of less than approximately 8 mm Hg (±S.D.). Thus, it is preferred that when dynamic pressure is applied in either a single or double needle configuration, the pressure difference between the first and second filter members is less than approximately 40, 30, 20, 15, 10, 8, or 5 mm Hg. Tests were also conducted with respect to penetration and rupture, resulting in no physiological solution penetration of the filter membranes of the device up to approximately 400 mm Hg, and no membrane rupture up to approximately 1500 mm Hg.

Figure 3:
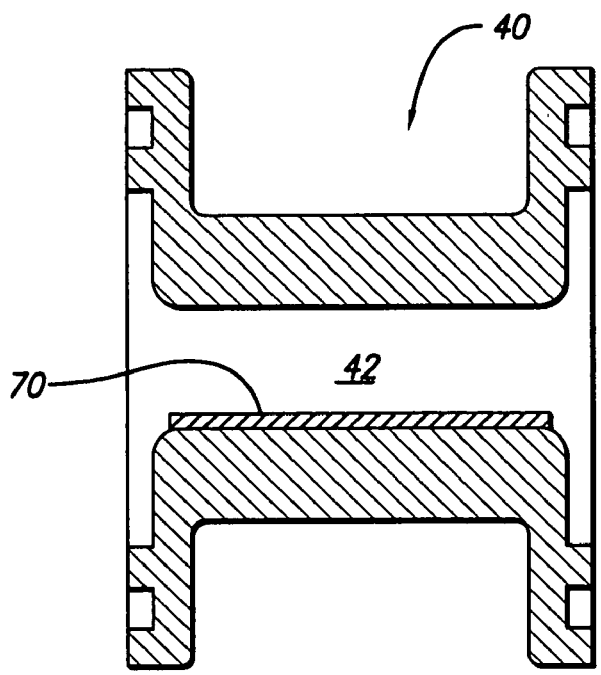
FIG. 3 is a view, in isolation, of the body of the transducer protector of FIG. 1, illustrating another embodiment.
Figure 4:
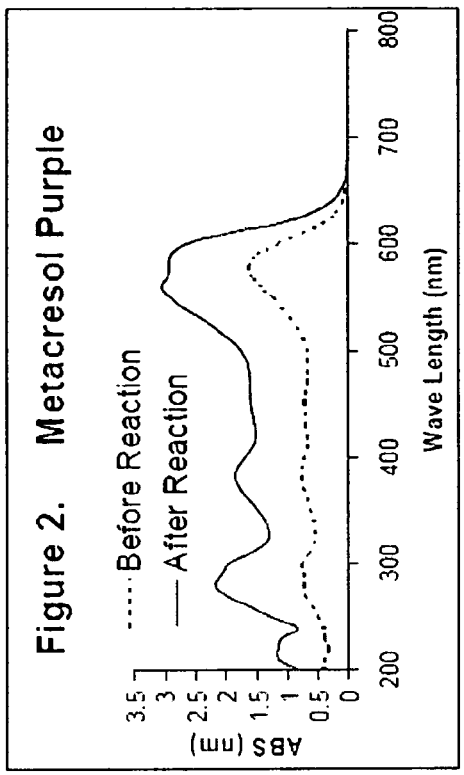
FIGS. 4A-4D show the absorption spectra for (A) Indigo Carmine, (B) m-cresol purple, (C) Neutral Red, and (D) Brilliant Blue G250, before and after reaction with BSA in an aqueous solution.
Figure 4:
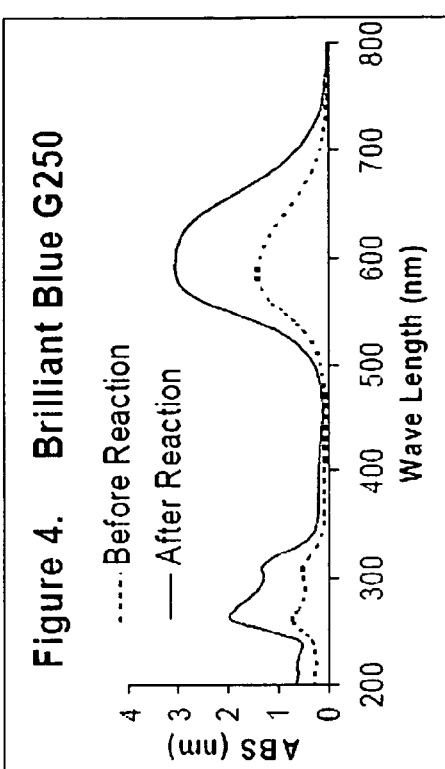
Figure 4:
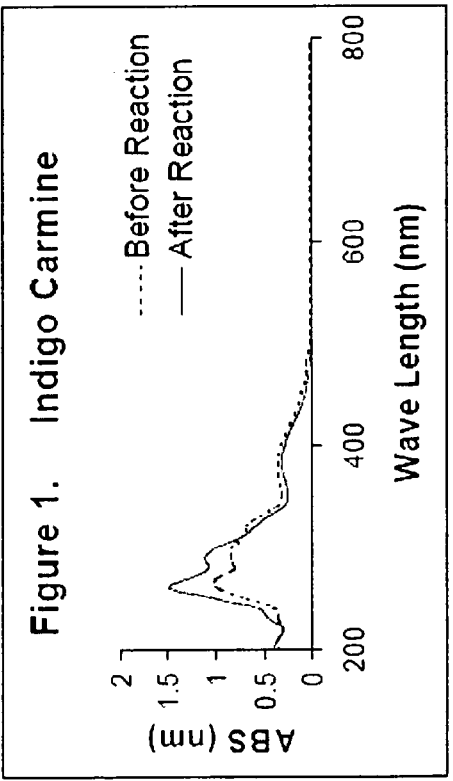
Figure 4:
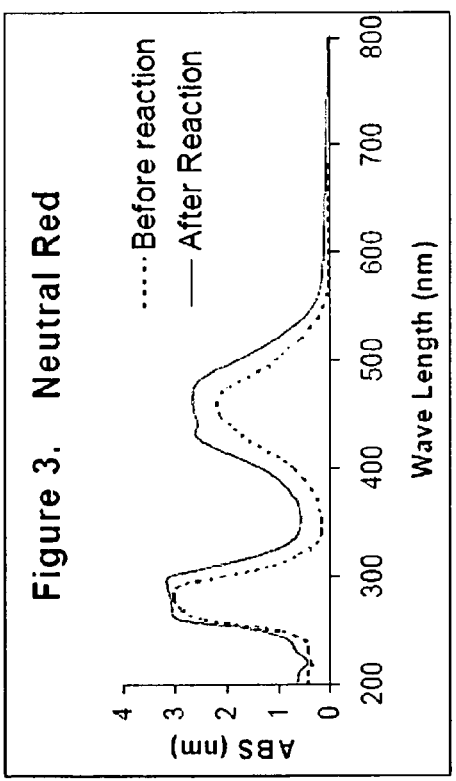

Referring to FIG. 3, furthering the goal of providing a means of detection for a clinician or physician monitoring a dialysis system, an embodiment is shown in which an inner wall of the body 40 defining body lumen 42 has a coating 70 thereon to assist in providing a signal to the clinician or physician regarding fluid or airborne pathogens that have progressed beyond the filter membrane 50. The coating could, for example, immediately change color upon contact with a contaminant, such as blood, to provide the signal to the clinician. Of course, many different materials would be possible for the coating 70, as would be apparent to one of skill in the art, which could provide a number of different indicators other than a color change. While the coating is shown on a certain section of a wall of the body 40 defining body lumen 42, certainly as necessary, the entire circumference of the wall could be coated. Likewise, although a majority of the length of the wall defining body lumen 42 is shown with a coating 70 thereon, it should be appreciated that smaller or longer segments of the wall could be coated, depending on the particular materials used and/or the application involved. Moreover, while a coating 70 is shown, various different chemical or biological indicators are also possible in place of or in addition to the coating 70, as would be apparent to one of skill in the art.

With respect to a coating that changes color upon contact with a contaminant, experimentation was conducted to determine preferred dyes. Initially, the dyes chosen for further experimentation met criteria including safety, sensitivity to small amount of one or more blood components, observable by the naked eye upon contact with the blood components, and cost. Thereafter, dyes were further screened and chosen based on the writings of those skilled in the art, such as "A Simple Stained Protein Assay (SPA) for Rapid Total Protein Determination Applied to Spinal Fluid," by Wadsworth, C., Scand J. Immunol., 1976, 5(10): 1209-13, which is incorporated into this application as if fully set forth herein. The selection process narrowed the potential dyes to four: Indigo Carmine (5,5'-indigosulfonic acid), m-cresol purple, Neutral red, and Brilliant Blue G250. Three separate experiments were then conducted to determine the one or more preferred dyes for use with a transducer protector described herein.

In the first experiment, the dyes were tested for interaction with a blood protein, each of the dyes having an aqueous solution prepared as shown in Table 1, and tested for light absorbance at wavelengths of between approximately 200 nanometers and 800 nanometers.

TABLE 1

| DYE | CONCENTRATION |
| --- | --- |
| Indigo Carmine | 0.0025% in water, pH 13 |
| m-cresol purple | 0.0025% in 0.0105 M NaOH, pH 10 |
| Neutral red | 0.0015% in 50/50 IPA/water, pH 10 |
| Brilliant Blue G250 | 0.0015% in water, pH 7.0 |

The solutions were subsequently reacted with a blood protein by mixing 995 microliters of each with 5 microliters of 5% Bovine Serum Albumin (BSA) for approximately 10 minutes, and tested for light absorbance at the same wavelengths of between approximately 200 nanometers and 800 nanometers. The results of the testing are shown in FIGS. 4A-4D. The increased optical density following the reaction with BSA in each of the dyes appears to indicate that a blood component contaminated spot on an area of a transducer protector coated with one or more of the dyes will be observable by a clinician.

Subsequently, the sensitivity of each dye to a blood component was evaluated. Filter paper was impregnated with each of the dyes. After drying, drops of BSA were dropped onto the filter papers, and reaction with each dye noted. BSA was used at varying concentrations (5%, 0.5%, 0.05%, 0.005%, and 0.0005%) and volumes (1, 2.5, and 5 microliters). Sensitivity was indicated by a combination of concentration and volume of the blood protein.

M-cresol purple and neutral Red reacted with BSA in solid phase: the color contrast upon reaction of each dye with BSA was vivid. In both cases, the sensitivity detected 1 microliter of BSA at a 0.0005% dilution. Indigo carmine and Brilliant Blue G250 did not react with BSA as well: the color contrast was not enough for visual detection. The results appear to indicate that a blood component contaminated spot on an area of a transducer protector coated with one or more of the dyes will be observable by a clinician.

The interaction with each of the four dyes with human plasma was then examined. The interior of polypropylene coupons were coated with coating formula containing each of the dyes. Human plasma was prepared at 1×, 10×, 100×, 1000×, and 10,000× dilutions. 1, 2.5, and 5 microliter drops of each diluted human plasma solutions were dropped on the interior surface of the coated polypropylene coupons.

M-cresol purple, indigo carmine, and Brilliant Blue 250 all reacted well with human plasma. The color contrast between unreacted and reacted dye was vivid on the interior surface of the polypropylene coupon. Under the coating conditions of the experiment, however, only m-cresol purple coating had a strong contrast between the reacted and unreacted areas that was easily observable on the exterior of the coupon. The m-cresol purple coating could detect the presence of 1 microliter of human plasma at a 10,000× dilution. The results appear to indicate that one or more blood components contained in human plasma will react with one or more of the selected dyes coated on an area of a transducer protector and that said reaction will be observable by a clinician. It should be appreciated, however, that while preferred dyes are mentioned, certainly other dyes are possible for the coating and are within the scope of the invention.

Figure 5:
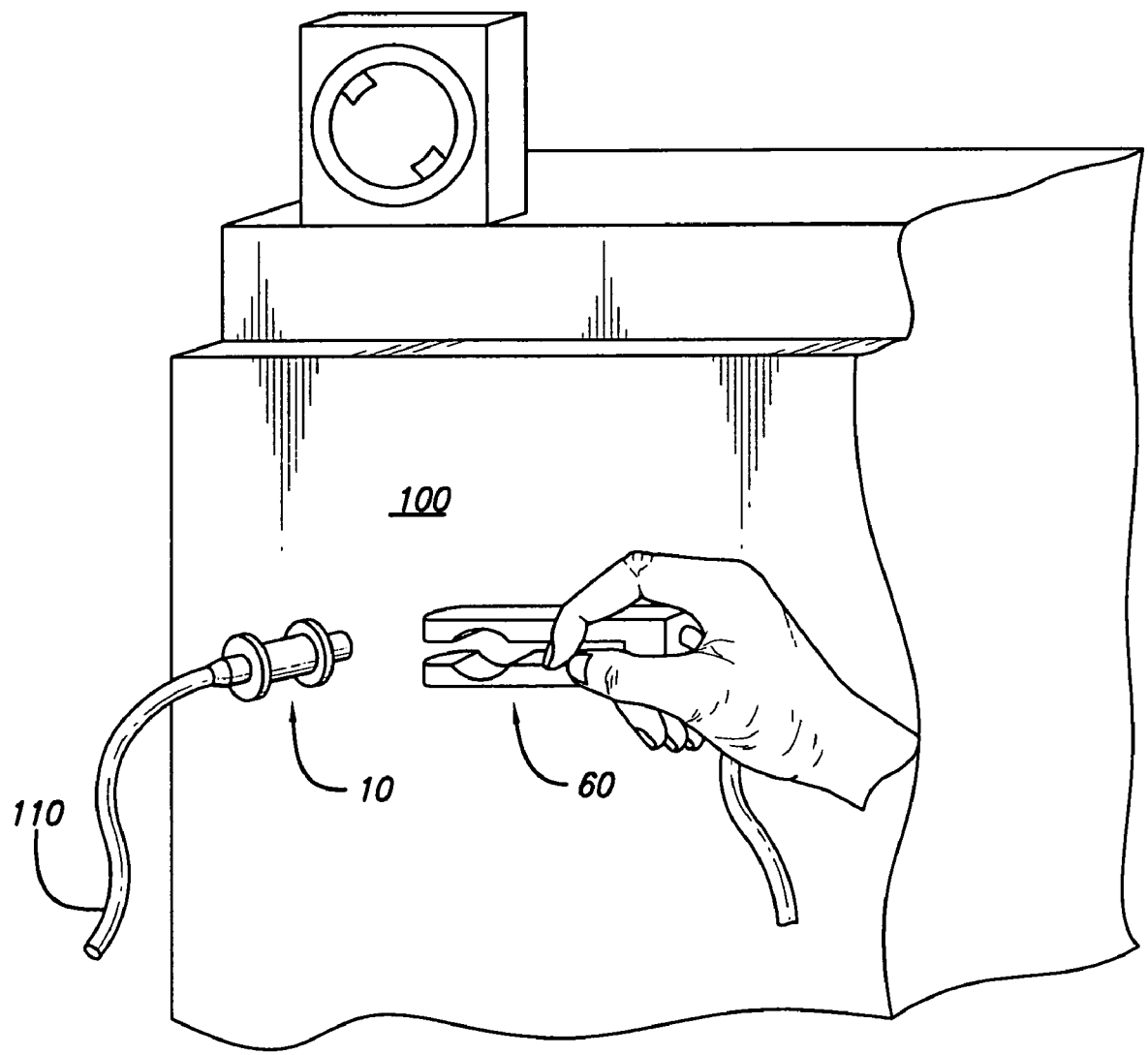
FIG. 5 is a perspective view of the transducer protector of FIG. 1 attached to a dialysis machine, illustrating the use of a sensor clip therewith.

FIG. 5 illustrates a further means of monitoring the transducer protector 10. In this embodiment, the transducer protector 10 is attached to a dialysis machine 100 on one side and to a monitoring line 110 of a blood tubing set on the opposite side. A sensor clip 60 is then clipped to the body 40. The sensor clip 60 utilizes optical or other means to detect whether a contaminant is present in the body lumen 42 after having breached the filter membrane separating the monitoring line 110 from the body 40. Once a contaminant is detected, a signal is immediately transmitted to a warning device, which can be incorporated into a dialysis machine or can be a stand alone device, which alerts the clinician that a breach has occurred. Due to the dual membrane properties of the transducer protector 10, the clinician is able to prevent the contaminant from reaching the dialysis machine 100. It should be understood that the sensor clip 60 could be used in combination with or instead of any of the aforementioned means of detection.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A transducer protector device, comprising:
   a first connector configured for connection to a first tube;
   a second connector configured for connection to a second tube;
   a body including a lumen positioned between the first and second connectors, a first filter member having a portion captured between a first surface of the body and the first connector, and a second filter member having a portion captured between a second surface of the body and the second connector; and
   an indicator disposed in the body, the indicator displaying a change in an absorbance spectra peak at a wavelength ranging from approximately 200 nm to approximately 800 nm upon reacting with bodily fluid.

2. The device according to claim 1, wherein the body includes a transparent or translucent material.

3. The device according to claim 1, wherein the bodily fluid comprises a blood component.

4. The device according to claim 3, wherein the indicator shows a change in absorbance intensity in a peak upon reacting with a blood component.

5. The device according to claim 3, wherein the indicator shows an increase in absorbance intensity in a peak upon reacting with a blood component.

6. The device according to claim 3, wherein the indicator shows a change in absorbance wavelength in a peak upon reacting with a blood component.

7. The device according to claim 1, wherein the indicator is selected from the group consisting of m-cresol purple, Indigo Carmine, and Brilliant Blue G250.

8. The device according to claim 1, wherein the indicator comprises a coating on an inner surface of the body.

9. The device according to claim 1, wherein the absorbance spectra peak is at a wavelength ranging from approximately 380 nm to approximately 780 nm.

10. The device of claim 1, wherein the body and the first and second connectors are hermetically sealed together.

11. The device according to claim 1, wherein the body is ultrasonically welded to the first and second connectors.

12. The device according to claim 1, wherein the distance between the first and second filter members is in the range of approximately 1 mm to approximately 20 mm.

13. The device according to claim 1, wherein at least one of the first and second filter members is comprised of a material selected from the group consisting of PTFE, PES, PVDF, acrylic copolymer, or polypropylene and combinations thereof.

14. A transducer protector device, comprising:
   a housing including spaced apart first and second filter members; and
   an indicator disposed in the housing between the filter members, the indicator displaying a change in an absorbance spectra peak at a wavelength ranging from approximately 200 nm to approximately 800 nm upon reacting with bodily fluid.

15. The device according to claim 14, wherein the indicator comprises a biological or chemical indicator.

16. The device according to claim 14, whereby the bodily fluid comprises a blood component.

17. The device according to claim 16, wherein the indicator shows an increase in absorbance intensity in a peak upon reacting with a blood component.

18. The device according to claim 14, wherein the indicator is m-cresol purple.

19. The device according to claim 14, wherein the indicator reacts with approximately 1 microliter of the bodily fluid.

20. The device according to claim 14, wherein at least one of the first and second filter members is comprised of a material selected from the group consisting of PTFE, PES, PVDF, acrylic copolymer, or polypropylene and combinations thereof.

* * * * *